United States Patent
Funk et al.

(10) Patent No.: US 7,351,302 B2
(45) Date of Patent: Apr. 1, 2008

(54) METHOD FOR BINDING PARTICULATE, WATER-ABSORBING, ACID GROUP-CONTAINING POLYMERS TO A BASE MATERIAL

(75) Inventors: Rüdiger Funk, Niedernhausen (DE); Ulrike Hoss, Kriftel (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/514,934

(22) PCT Filed: Jun. 6, 2003

(86) PCT No.: PCT/EP03/05939

§ 371 (c)(1),
(2), (4) Date: Nov. 12, 2004

(87) PCT Pub. No.: WO03/104543

PCT Pub. Date: Dec. 18, 2003

(65) Prior Publication Data

US 2006/0025030 A1    Feb. 2, 2006

(30) Foreign Application Priority Data

Jun. 11, 2002  (DE) .............. 102 25 944

(51) Int. Cl.
B32B 37/24   (2006.01)
B05D 7/24    (2006.01)

(52) U.S. Cl. ............... 156/279; 156/62.6; 156/305; 427/180; 427/203

(58) Field of Classification Search ........... 156/279
See application file for complete search history.

(56) References Cited

U.S. PATENT DOCUMENTS

| | | | | |
|---|---|---|---|---|
| 4,270,977 A | * | 6/1981 | Herman et al. | 162/168.7 |
| 4,401,795 A | * | 8/1983 | Herman et al. | 525/327.8 |
| 4,654,039 A | * | 3/1987 | Brandt et al. | 604/368 |
| 5,102,597 A | * | 4/1992 | Roe et al. | 264/126 |
| 5,120,364 A | * | 6/1992 | Karydas et al. | 106/287.23 |
| 5,292,853 A | * | 3/1994 | Yasuda et al. | 528/72 |
| 5,352,480 A | * | 10/1994 | Hansen et al. | 427/202 |
| 5,387,483 A | * | 2/1995 | Takagi | 430/204 |
| 5,589,256 A | | 12/1996 | Hansen et al. | |
| 5,807,364 A | * | 9/1998 | Hansen | 604/367 |
| 5,977,014 A | * | 11/1999 | Plischke et al. | 502/401 |
| 6,060,557 A | * | 5/2000 | Dahmen et al. | 524/556 |
| 6,099,950 A | | 8/2000 | Wang et al. | |
| 6,174,929 B1 | * | 1/2001 | Hahnle et al. | 521/64 |
| 6,184,310 B1 | * | 2/2001 | Utecht et al. | 525/359.4 |
| 6,455,600 B1 | | 9/2002 | Hahnle et al. | |
| 6,461,553 B1 | * | 10/2002 | Hansen et al. | 264/122 |
| 6,794,436 B2 | * | 9/2004 | Schlarb et al. | 524/423 |
| 2002/0091366 A1 | * | 7/2002 | Abrahamsson | 604/368 |
| 2003/0121857 A1 | * | 7/2003 | Kurth et al. | 210/651 |
| 2005/0131367 A1 | * | 6/2005 | Sun et al. | 604/367 |

FOREIGN PATENT DOCUMENTS

| | | |
|---|---|---|
| EP | 2 205 674 | 12/1986 |
| EP | 0 442 185 | 8/1991 |
| WO | WO 94/04351 | 3/1994 |
| WO | WO 94/04352 | 3/1994 |
| WO | WO 99/44648 | 9/1999 |
| WO | WO 01/56625 | 8/2001 |

* cited by examiner

*Primary Examiner*—Melvin Mayes
(74) *Attorney, Agent, or Firm*—Marshall, Gerstein & Borun LLP

(57) ABSTRACT

A process for binding particulate water-absorbing acid-functional polymers to a carrier material by means of compounds comprising amino groups, which comprises contacting the carrier material with particulate water-absorbing acid-functional polymers whose acid groups have been 0 to not more than 55 mol % neutralized with alkali metal and/or ammonium bases and then raising the degree of neutralization of these polymers to not less than 60 mol % by treatment with amino-containing compounds. The use of compounds comprising amino groups and selected from the group of the compounds consisting of the alkanolamines and compounds which contain ethyleneimine and/or vinylamine units to neutralize and bind particulate water-absorbing acid-functional polymers neutralized 0 to not more than 55 mol % with alkali metal and/or ammonium bases to a carrier material.

11 Claims, No Drawings

METHOD FOR BINDING PARTICULATE, WATER-ABSORBING, ACID GROUP-CONTAINING POLYMERS TO A BASE MATERIAL

CROSS REFERENCE TO RELATED APPLICATION

This is the U.S. national phase application of International Application No. PCT/EP03/05939, filed Jun. 6, 2003, which claims the benefit of German patent application No. 102 25 944.5, filed Jun. 11, 2002.

DESCRIPTION

The present invention relates to a process for binding particulate water-absorbing crosslinked polymers containing acid groups to a carrier material by means of compounds comprising amino groups.

Particulate water-absorbing crosslinked polymers which contain acid groups and are capable of absorbing a multiple of their owns weight of water are known as superabsorbent polymers (SAPs) or simply superabsorbents. They are used for example in hygiene articles such as diapers, tampons or dressings to absorb body fluids. The particulate superabsorbents consist for example of crosslinked polyacrylic acids which are at least 50 mol % neutralized. The surface of the particles has usually been postcrosslinked. When hygiene articles are handled or used, the superabsorbents present therein can become separated from the cellulose fibers, so that they are no longer uniformly distributed in the hygiene article. But this adversely affects the uptake capacity and uptake rate of body fluids. To bind particulate superabsorbents in a hygiene article to the cellulose fibers and thereby to fix them, polyaluminum chloride has already been used as a binder, cf. EP-A-0 442 185.

U.S. Pat. No. 5,589,256 discloses fixing particulate superabsorbents to fibers, preferably cellulose fibers, by means of polymeric and non-polymeric binders and to process the mixture into webs. Suitable binders are for example polypropylene glycol, polyacrylic acid, polyglycine, polyethyleneimine, polyvinylpyridine, butanediol, ethanolamine, propylene glycol and ascorbic acid. Webs where a superabsorbent has been bound to cellulose fibers by means of a binder can if desired be densified by the action of pressures, for example in a calender. This gives relatively thin absorbent articles which are used in hygiene articles for example.

U.S. Pat. No. 6,099,950 discloses absorbent polymers having improved absorbent properties. The polymers have been surface postcrosslinked and coated with a cationic polymer which has an average molecular weight of at least 500. Suitable cationic polymers are for example polyvinylamines, polyallylamines, polyethyleneimines and modified polyethyleneimines. As is evident from the examples, polyallylamine is used as a cationic polymer.

The superabsorbents treated with polyallylamine have distinctly enhanced salt flow conductivity (SFC) and ball burst strength (BBS) values and a lower level of extractable fractions compared with the untreated superabsorbents.

WO-A-99/44648 discloses open-cell foams formed from crosslinked polyacrylates whose acid groups have been at least 20 mol % neutralized with an alkanolamine after polymerization. Such foams are soft and flexible. However, their surface is tacky. To control tackiness, they are-usually coated with finely divided powders such as silicon dioxide, talcum or silicates.

The present invention has for its object to provide a further process for binding particulate water-absorbing acid-functional polymers to a carrier material whereby ideally a stronger bond of the polymeric particles to the carrier material is obtained compared with existing processes.

We have found that this object is achieved according to the present invention by a process for binding particulate water-absorbing acid-functional polymers to a carrier material by means of compounds comprising amino groups, which comprises contacting the carrier material with particulate water-absorbing acid-functional polymers whose acid groups have been 0 to not more than 55 mol % neutralized with alkali metal and/or ammonium bases and then raising the degree of neutralization of these polymers to not less than 60 mol % by treatment with amino-containing compounds.

Another aspect of the invention is the use of compounds comprising amino groups and selected from the group of the compounds consisting of the alkanolamines and compounds which contain ethyleneimine and/or vinylamine units to neutralize and bind particulate water-absorbing acid-functional polymers, neutralized 0 to not more than 55 mol % with alkali metal and/or ammonium bases, to a carrier material.

The starting materials used are usually such particulate water-absorbing acid-functional crosslinked polymers (particulate SAPs) as have their acid groups less than 50 mol % neutralized. The particulate SAPs which are initially contacted with a carrier material preferably have a degree of neutralization in the range from 0 to 45 mol %. The degree of neutralization of the particulate SAPs is more preferably in the range from 15 to 40 mol %. It is also possible to use non-neutralized particulate SAPS with advantage, i.e., particulate SAPS where all the acid groups are present in the form of free carboxyl groups.

Particulate water-absorbing acid-functional crosslinked polymers whose acid groups are 0 to not more than 55 mol % neutralized with alkali metal and/or ammonium bases are known, cf. EP-A-0 205 674, EP-A-0 530 438 and U.S. Pat. No. 5,145,906. Such particulate SAPS are obtainable for example by polymerizing acid-functional monomers in non-neutralized or in partially neutralized form in the presence of a crosslinker and of a polymerization initiator in an aqueous medium and comminuting the resulting hydrogel. If the acid-functional monomers used in the polymerization do not have the degree of neutralization which the SAPS to be used according to the present invention are supposed to have, the gels obtained in the course of the polymerization can be neutralized by reaction with alkali metal bases and/or ammonium bases. The alkali metal bases used are preferably aqueous sodium hydroxide solution or aqueous potassium hydroxide solution. Suitable ammonium bases are for example ammonia, primary, secondary and/or tertiary amines.

To produce hydrogels having improved absorbent properties and improved mechanical stability, it will be known that particulate SAPs are subjected to a surface-postcrosslinking preparation, cf. for example U.S. Pat. No. 5,145,906 and U.S. Pat. No. 5,945,495. Suitable acid-functional monomers for producing SAPS are identified for example in column 5 of U.S. Pat. No. 5,945,495. A particularly preferred monomer of this kind is acrylic acid. As well as the polymers obtainable by polymerizing the monomers underlying the SAPs it is also possible to use graft polymers of acid-functional monomers on for example. polysaccharides such as starch or polyalkylene glycols or hydrophilic polyesters, cf. columns 5 and 6 of U.S. Pat. No. 5,945,495.

Preferably used particulate SAPS are surface-post-crosslinked particulate crosslinked polyacrylic acids having a degree of neutralization in the range from 0 to not more than 55 mol % and preferably up to less than 50 mol %. The pH of the particulate SAPs is for example in the range from 3 to 6, preferably in the range from 4 to 5.7 and more preferably in the range from 4.5 to 5.5.

The average particle diameter of the particulate SAPs is for example in the range from 50 to 2000 μm, preferably in the range from 100 to 850 μm and especially in the range from 150 to 700 μm.

The above-described particulate SAPs having a degree of neutralization of not more than 55 mol % are bound to a carrier material. Suitable carrier materials include any matrix capable of accommodating the highly swellable particulate SAPs. An example thereof is a matrix composed of fibers, for example natural and/or synthetic fibers. The fibers can be for example mixed with the particulate SAPs and processed in the form of the mixture to form a web. However, the particulate SAPs can also be incorporated in a web which consists for example of cellulose fibers or a mixture of cellulose fibers and synthetic fibers. It is similarly possible to process the particulate SAPs with fibers or webs in each case from synthetic polymers as a carrier material to form a matrix. Suitable carrier materials further include open-pore foams formed for example from melamine-formaldehyde condensates, aliphatic polyurethanes or crosslinked polyacrylates. It is also possible to use films/sheets composed of various materials such as polyethylene, polypropylene, polyamides or polyurethanes as carrier materials. Preference is given to using cellulose fibers and webs composed of cellulose fibers as a carrier material. As well as webs it is also possible to use wovens or tissues as a carrier material, which can be water pervious or else water impervious.

Useful carrier materials further include composite materials, formed for example by compositing together at least two films/sheets, wovens or webs. The composites in question may be constructed such that they have a multiplicity of pockets which are capable of accommodating the particulate SAPs. A two-layered composite can consist for example of a water-impervious film/sheet of polyethylene or polypropylene and a layer of web of cellulose fibers and contain the particulate SAPs between the two layers. It is similarly possible to have composites whose upper and lower surfaces consist of cellulose fibers for example and which contain particulate SAPs in uniform or else in heterogeneous distribution between the two plies or in the two webs. Processes for producing such composite materials are known. Production can be either batchwise or continuous.

The fraction of particulate SAPs in the combination formed from carrier material and SAP is for example in the range from 30% to 95% and preferably in the range from 50% to 95% by weight and is more preferably in the range from 60% to 95% and mostly in the 40 range from 80% to 95% by weight. Combinations having a particularly high storage effect with regard to aqueous fluids comprise for example an amount of particulate SAPs in the range from 90% to 95% by weight.

The particulate SAPs are bound to a carrier material by treatment with amino-containing compounds, which give an alkaline reaction, to raise the degree of neutralization of the particulate SAP used according to the present invention to not less than 60 mol %. Useful amino-containing compounds include for example alkanolamines.

The alkanolamines used can be primary, secondary, tertiary or quaternary in their structure and constitute monoacid, polyacid or polyfunctional bases. The alkanolamines, as well as their amino and hydroxyl groups, may bear further functional groups such as for example ester group, urethane group, ether group, thioether group, urea group, etc. It is possible to use, for example., low molecular weight compounds such as triethanolamine, methyldiethanolamine, dimethylethanolamine, ethanolamine, N-hydroxyethylmorpholine, dimethylaminodiglycol, N,N,N',N'-tetra-(hydroxyethyl)ethylenediamine, N,N,N',N'N-tetra(hydroxypropyl)-ethylenediamine, dimethylaminotriglycol, diethylaminoethanol, 3-dimethylamino-1,2-propanediol, triisopropanolamine, diisopropylaminoethanbl, choline hydroxide, choline carbonate, 2-tert-butylaminoethanol, tris(oxymethyl)aminomethane, 3-amino-1-propanol, isopropanolamine, 2-(2-aminoethoxy)ethanol, 2-amino-2-methyl-1-propanol or else oligomers or polymers obtainable by reaction of amino-functional addition polymers or condensates such as for example polyethyleneimines or polyvinylamines with ethylene oxide, propylene oxide, glycidol or other epoxides.

Preference is given to using triethanolamine, methyldiethanolamine, dimethylaminodiglycol, dimethylethanolamine, ethanolamine, N,N,N',N'-tetra(hydroxyethyl)ethylenediamine or mixtures thereof. Particular preference is given to using triethanolamine.

Useful amino-containing compounds, which give an alkaline reaction, further include polymers, for example polymers containing ethyleneimine units and/or vinylamine units. Polymers containing ethyleneimine units are prepared for example by polymerizing ethyleneimine in aqueous medium in the presence of acidic catalysts or by grafting for example polyamidoamines with ethyleneimine. Polymers containing vinylamine units are prepared by hydrolysis of polymers which contain interpolymerized units derived from open-chain N-vinylcarboxamide such as N-vinylformamide or N-vinylacetamide. cf. U.S. Pat. No. 4,421,602, U.S. Pat. No. 5,334,287, EP-A-0 216 387, U.S. Pat. No. 5,981,689, WO-A-00/63295 and U.S. Pat. No. 6,121,409. Preferably, homopolymers of N-vinylformamide are hydrolyzed to detach for example 5 to 100 mol % of formyl groups to form addition polymers containing vinylamine units.

The molar masses Mw of the abovementioned polymers are not less than 300 and mostly not less than 500. The molar masses Mw of the polyethyleneimines and of the polymers containing vinylamine units is preferably in the range from 1000 to 2 million and especially in the range from 1500 to 500 000.

To bind particulate SAPs to a carrier material, the initial step is to contact the carrier material with particulate water-absorbing acid-functional polymers whose acid groups are 0 to not more than 55 mol % neutralized with alkali metal and/or ammonium bases and then to raise the degree of neutralization of these polymers to not less than 60 mol % by treatment with amino-containing compounds. For example, particulate SAPs having a degree of neutralization in the range from 0 to 55 mol % can be applied to a web of natural and/or synthetic fibers before the degree of neutralization of the particulate SAPs is raised to not less than 60 mol %.by spraying with a solution of an amino-containing compound. This tackifies the particulate SAP and causes it to adhere to the fibers with which it is in contact. The process of the present invention makes it possible to produce all known hygiene articles by treating the absorbent core present in the hygiene article, provided it comprises particulate SAP having a degree of neutralization of not more than 55 mol %, with a basic, amino-containing compound such that the degree of neutralization of the particulate SAPs is raised to not less than 60 mol %.

The amino-containing compounds used for neutralization are preferably used in the form of solutions. Suitable solvents are for example water, alcohols such as methanol, ethanol, isopropanol, n-propanol and tert-butanol, ketones such as acetone or methyl ethyl ketones, esters such as ethyl acetate or ethers such as dioxane or tetrahydrofuran. It will be advantageous in some cases to use mixtures of two or more solvents for the binders, for example mixtures of water and ethanol, mixtures of water and isopropanol or mixtures of water and acetone. Water is the preferred solvent. The concentration of binder in the solvent or solvent mixture is for example in the range from 1% to 100% and preferably in the range from 70% to 95% by weight. When the binder used is liquid, as is the case with triethanolamine for example, the binder is preferably used without solvent.

Hygiene articles, as well as particulate SAPs, may further incorporate for example odor control agents. Such substances can be bound to the particulate absorbent polymers, and hence to the carrier materials, by the process of the present invention. Here it is advantageous to use particulate agents which effect odor control in use of the hygiene article, examples being inorganic substances having a large surface area such as finely divided, amorphous polysilicas (Aerosil□), bentonites, zeolites and activated carbon. It is also possible to use the known organic odor inhibitors such as cyclodextrins etc. in the customarily employed amounts.

After the treatment of the absorbent composition, which consists at least of a carrier material and a particulate SAP having a degree of neutralization in the range from 0 to 55 mol %, with a binder, preferably triethanolamine, the absorbent composition is dried by means of conventional techniques, for example through the action of infrared radiation, by heating with microwave irradiation or heating in a hot gas stream or—additionally, if appropriate—setting a reduced pressure. To remove the solvents from the absorbent composition, the material is heated for example to temperatures in the range from 50 to 120 □C.

However, the absorbent composition can also be heated, additionally if appropriate, to still higher temperatures whereby the dimensional stability of the absorbent layer in the moist state can be further improved. This form of heat treatment is carried out for example with a hot gas stream or by irradiating with infrared radiation at temperatures up to 230 □C. The temperatures in the course of heat treatment of the composite materials are preferably in the range from 100 to 200 □C. and especially in the range from 100 to 180 □C. The duration of the heat treatment depends on various factors, for example the identity of the synthetic fibers, the makeup of the mixture of particulate SAP and carrier material and the manufacturing speed of the hygiene article. The duration of the heat treatment is for example in the range from 0.5 seconds to 3 minutes and is mostly in the range from 1 second to 1 minute.

The process of the present invention is preferably integrated in the manufacturing operation of the hygiene article, in which case the degree of neutralization of the particulate SAPs is effected only after incorporation of the particulate SAPs in the composite or concurrently with the bringing together of particulate SAPs and carrier material. Known hygiene articles have for example the following construction:

(A) a liquid-pervious topsheet (B) a liquid-impervious backsheet (C) a core which is situated between (A) and (B) and comprises
  (i) 10-100% by weight of the hydrogel-molding polymer
  (ii) 0-90% by weight of hydrophilic fibrous material (D) if appropriate, a tissue layer situated directly above and below the core (C), and (E) if appropriate, an acquisition layer situated between (A) and (C).

Hygiene articles for the purposes of the present invention include not only incontinence pads and incontinence briefs for adults but also diapers for infants.

The liquid-pervious topsheet (A) is the layer which is in direct contact with the skin. Its material consists of customary synthetic or manufactured natural-polymer fibers or films of polyester, polyolefins, rayon or natural fibers such as cotton. In the case of non-woven materials the fibers are generally joined together by binders such as polyacrylates. Preferred materials are polyesters,-rayon and blends thereof, polyethylene and polypropylene.

The liquid-impervious layer (B) consists in general of a film/sheet of polyethylene or polypropylene.

The core (C), as well as the hydrogel-molding polymer (i) of the present invention, contains hydrophilic fibrous material (ii). By hydrophilic is meant that aqueous fluids spread quickly over the fiber. The fiber material is usually cellulose, modified cellulose, rayon, polyester such as polyethylene terephthalate. Particular preference is given to cellulose fibers such as chemical pulp. The fibers generally have a diameter of 1-200 µm and preferably 10-100 µm. The fibers also have a minimum length of 1 mm.

The fraction contributed by the hydrophilic fibrous material to the total amount of the core is preferably 20-80% by weight and more preferably 40-70% by weight. Such diapers are described for example in EP-A-0 316 518.

Through the firm attachment of the particulate SAPs and if appropriate of further constituents to the carrier material the absorbent compositions produced by the process of the present invention possess remarkable stability in the dry state and in the wet state. A particulate absorbent material which has been attached in a hygiene article by the method of the present invention does not dislodge in the course of the use or transportation of the hygiene article. The hygiene article possesses a high level of wet integrity and dimensional stability. Absorbent particulate polymers incorporated in high concentration possess high absorbency, gel strength, permeability and retention. They also have improved odor properties in use of the hygiene articles. Since the pH of the particulate SAPs after attachment in the hygiene article is below 7.0, the absorbent polymers have an antimicrobial action, so that there is in most cases no need to add odor-inhibiting substances. The almost unchanging pH in the superabsorbent means that skin sensitizations and skin irritations are practically avoided in use of the hygiene articles.

Test Methods

Centrifuge Retention Capacity (CRC)

This method measures the free swellability of the hydrogel in a teabag. To determine CRC, 0.2000±0.0050 g of dried hydrogel (particle size fraction 106-850 µm) are weighed into a teabag 60×85 mm in size, which is subsequently sealed. The teabag is placed for 30 minutes in an excess of 0.9% by weight sodium chloride solution (at least 0.83 l of sodium chloride solution/l g of polymer powder.

The teabag is then centrifuged at 250 g for 3 minutes. The amount of liquid is determined by weighing back the centrifuged teabag.

Absorbency Under Load (AUL) (0.7 psi)

The measuring cell for determining AUL 0.7 psi is a Plexiglas cylinder 60 mm in internal diameter and 50 mm in height. Adhesively attached to its underside is a stainless steel sieve bottom having a mesh size of 36 µm. The measuring cell further includes a plastic plate having a diameter of 59 mm and a weight which can be placed in the measuring cell together with the plastic plate. The plastic plate and the weight together weigh 1345 g. AUL 0.7 psi is determined by determining the weight of the empty Plexiglas cylinder and of the plastic plate and recording it as WO. 0.900±0.005 g of hydro-molding polymer (particle size distribution 150-800 µm) is then weighed into the Plexiglas cylinder and distributed very uniformly over the stainless steel sieve bottom. The plastic plate is then carefully placed in the plastic cylinder, the entire unit is weighed and the weight is recorded as $W_a$. The weight is then placed on the plastic plate in the Plexiglas cylinder. A ceramic filter plate 120 mm in diameter and 0 in porosity is then placed in the middle of a Petri dish 200 mm in diameter and 30 mm in height and sufficient 0.9% by weight, sodium chloride solution is introduced for the surface of the liquid to be level with the filter plate surface without the surface of the filter plate being wetted. A round filter paper 90 mm in diameter and <20 µm in pore size (S&S 589 Schwarzband from Schleicher & Schüll) is subsequently placed on the ceramic plate. The Plexiglas cylinder containing hydrogel-molding polymer is then placed with the plastic plate and the weight on top of the filter paper and left there for 60 minutes. At the end of this period, the complete unit is taken from the filter paper and out of the Petri dish and subsequently the weight is removed from the Plexiglas cylinder. The Plexiglas cylinder containing swollen hydrogel is weighed together with the plastic plate and the weight is recorded as $W_b$.

Absorbency under load (AUL) is calculated as follows:

AUL 0.7 psi $[g/g]=[W_b-W_a]/[W_a-W_0]$

Saline Flow Conductivity (SFC)

The test method for determining SFC is in U.S. Pat. No. 5,599,335.

Measuring the pH of Hydrogel-Molding Polymers 100 ml of 0.9% by weight NaCl solution is magnetically stirred in a 150 ml glass beaker at a moderate speed, so that no air is drawn into the solution by the stirring. To this solution is added 0.5±0.001 g of hydrogel-molding polymer and stirred for 10 minutes. After 10 minutes, the pH of the solution is measured by means of a pH glass electrode, the value not being read off until it is stable, but at the earliest after 1 minute.

Ammonia Determination for Odor Control

The ammonia nitrogen content is determined calorimetrically by the Nessler method. The measurement was carried out on a DR/2000 spectrometer from Hach Company, Loveland, Colo. 80539, USA.

5 g of the various superabsorbent samples were drenched with 600 ml of a 0.9% NaCl and 1.8% urea solution for 20 min. The solutions were filtered off and 25 ml of the solution was admixed with 10 µl of urease solution. After 2 minutes, nitrogen from ammonia was determined by the Nessler method.

Urea eliminates ammonia under the action of urease; a yellow color develops to a degree proportional to the ammonia concentration. Since urease activity is strongly pH-dependent and maximum activity is attained at pH 6.1, a lower pH is likely to give lower ammonia evolution. A low ammonia concentration should thus be measurable in the case of acidic SAP.

Strength of Fixing of SAP to Fiber Matrix

To determine the degree of fixing of the superabsorbent polymeric material within the absorbent composition, pads were prepared in the laboratory from cellulose fiber material and highly swellable polymeric material (SAP). Not only acidic but also partially neutralized superabsorbent polymeric material was used. The average particle diameter of the particular SAPs used was in the range from 100 to 800 µm.

To determine the strength of fixing of the polymeric material to the fiber matrix, the pad was transferred into a Retsch sieving machine (sieve bottom: 2 mm mesh size) and shaken at a shaking intensity of 90% for a period of 5 minutes. The SAP sieved off was subsequently weighed. The percentage of particulate SAP in the pad after shaking served as a measure of the strength of fixing.

Production of Partially Neutral Particulate SAPs Polymer

Polymer I

A WERNER & PFLEIDERER laboratory kneader having a working capacity of 2 l was evacuated to 980 mbar absolute by means of a vacuum pump and a previously separately prepared monomer solution which had been cooled to about 25° C. and inertized by passing nitrogen into it was sucked into the kneader. The monomer solution was made-up as follows: 825.5 g of water, 431 g of acrylic acid, 120.68 g of NaOH 50%, 0.86 g of polyethylene glycol 400 diacrylate (SARTOMER® 344 from CRAY VALLEY). To improve the inertization, the kneader was evacuated and subsequently refilled with nitrogen. This operation was repeated three times. A solution of 1.2 g of sodium persulfate (dissolved in 6.8 g of completely ion-free water) was then sucked in, followed after a further 30 seconds by a further solution consisting of 0.024 g of ascorbic acid dissolved in 4.8 g of water. After a nitrogen purge a preheated jacket heating circuit on bypass at 75° C. was switched to the kneader jacket and the stirrer speed was increased to 96 rpm. Following the onset of polymerization and the attainment of $T_{max}$, the jacket heating circuit was switched back to bypass, and the batch was supplementarily polymerized for 15 minutes without heating/cooling, subsequently cooled and the product discharged. The resultant gel particles were dried at 160° C. on wire mesh bottomed trays in a forced-air drying cabinet at 160° C., and were subsequently ground and sieved.

1200 g of the thus obtained product of particle size distribution 105-850 µm were sprayed with a homogeneous solution of 17.58 g of water, 9.96 g of 1,2-propanediol, 1.2 g of ethylene glycol diglycidyl ether and 3.36 g of a 26.8% aqueous aluminum sulfate solution in a powder mixing assembly (Loedige mixer) and transferred into a preheated second Lödig mixer. The heat treatment was carried out under constant conditions at a jacket temperature of 150° C. and a speed of 60 rpm for a period of 70 minutes. The mixer was emptied, and the product was cooled down to room temperature and sieved off at 105/850 µm to remove any agglomerates or fines which may have formed. The performance data of the SAP are shown in Table 1.

Preparation of Partially Neutral Particulate SAPs

POLYMER II

The partially neutral high-swellable polymer is commercially available TYLOSE VS 3790 (lot./Avil 903642), a superabsorbent from CASSELLA AG of Frankfurt/Main, having a pH of 5-5.5 (prepared similarly to Example 7 of EP-B-0316792). The polymer was admixed on a 20 g scale in a WARNING blender (modified attachment for kitchen processor) with a surface-postcrosslinking solution (sprayed from a 2 ml syringe) consisting of 2.3% of water/1.2% of 1,2-propanediol/0.2% of ethylene glycol diglycidyl ether (each percentage being based on polymer) and heat treated in a forced-air drying cabinet at 140° C. for 1 hour. The performance data are reported in Table 1.

TABLE 1

|  | pH | SFC × $10^{-7}$ cm$^3$s/g | CRC g/g | AUL 0.7 psi g/g | N$_2$ from NH$_3$ (Nessler) mg/l | Degree of neutralization [mol %] |
|---|---|---|---|---|---|---|
| Polymer I | 4.3 | 13.8 | 20.7 | 18.1 | 1.8 | 25 |
| Polymer II | 5.4 | 17 | 32.9 | 23.0 | 5.6 | 45 |

Preparation of Pads

The apparatus used consisted of a rectangular Plexiglas vessel measuring 10×15 cm, which was sealed off at the bottom with a stainless steel sieve 1 mm in mesh size. A commercially available vacuum cleaner was attached below the stainless steel sieve to create an underpressure.

Preparation of Pads Having Homogeneous Plies

To produce homogeneous plies, 4 g of cellulose fiber material mixed with 6 g of highly swellable SAP were introduced all at once into the above-described apparatus under underpressure. The pad had a uniform thickness.

The parts reported in the examples are by weight, the %ages are weight percent, unless suggested otherwise by the context.

EXAMPLE 1

The method described above was followed to produce a pad having the following layering: 2 g of cellulose fiber material and 6 g of polymer I. This layering was subsequently sprayed with triethanolamine until the degree of neutralization of the carboxyl groups in polymer I was 80 mol % (pad 1). In a second step, 2 g of cellulose fiber material were introduced into the apparatus and likewise sprayed with triethanolamine (pad 2). Thereafter, pad 2 was placed with the sprayed side on pad 1 and this assembled pad was pressed twice at 200 bar for 15 s.

EXAMPLE 2

Example 1 was repeated with the single exception that the same amount of polymer II was used.

EXAMPLE 3

A pad having inhomogeneous layering was produced in the above-described apparatus by introducing a mixture of 2 g of cellulose fibers and 6 g of polymer I into the apparatus and then applying 2 g of cellulose fibers as a layer on top. Polymer I was neutralized up to a degree of neutralization of 80 mol % by spraying the layering with triethanolamine.

EXAMPLE 4

Example 1 was repeated with the single exception that the degree of neutralization of the carboxyl groups in polymer I was adjusted to 60 mol %.

EXAMPLE 5

A pad having homogeneous layering was produced in the above-described apparatus by introducing a mixture of 1 g of cellulose fibers and 8 g of polymer I into the apparatus and then applying 1 g of cellulose fibers as a layer on top. Polymer I was neutralized up to a degree of neutralization of 80 mol % by spraying the layering with triethanolamine.

COMPARATIVE EXAMPLE 1

Example 1 was repeated with the single exception that the carboxyl groups of polymer I were neutralized up to a degree of neutralization of 80 mol % by spraying the layering with 50% aqueous sodium hydroxide solution.

COMPARATIVE EXAMPLE 2

Example 2 was repeated with the single exception that 50% aqueous sodium hydroxide solution was used instead of an aqueous solution of triethanolamine and the carboxyl groups of polymer II were neutralized up to a degree of neutralization of 80%.

The composites produced according to the inventive and comparative examples were dried at a temperature of 80° C. and subsequently tested by the above-described method for the strength of the fixing of SAP particles. The results are reported in Table 2.

TABLE 2

| Example | Layering in pad | Polymer fraction in pad | Total degree of neutralization | Polymer fraction sieved off in sieve test |
|---|---|---|---|---|
| 1 | homogeneous | Polymer I, 60% | 80 mol % | 6% |
| 2 | homogeneous | Polymer II, 60% | 80 mol % | 11% |
| 3 | inhomogeneous | Polymer I, 60% | 80 mol % | 5% |
| 4 | homogeneous | Polymer I, 60% | 60 mol % | 9% |
| 5 | homogeneous | Polymer I, 80% | 80 mol % | 8% |
| Comparative Example 1 | homogeneous | Polymer I, 60% | 80 mol % | 35% |
| Comparative Example 2 | homogeneous | Polymer II, 60% | 80 mol % | 42% |

The invention claimed is:

1. A process for binding a particulate water-absorbing acid-functional polymer to a carrier material by means of a compound comprising amino groups, which comprises contacting the carrier material with a particulate water-absorbing acid-functional polymer whose acid groups are 15 to 55 mol % neutralized with an alkali metal and/or ammonium base and then applying the amino-containing compound to raise the degree of neutralization of the polymer to not less than 60 mol % by treatment, wherein the amino-containing compound is a compound containing vinylamine units.

2. The process according to claim 1 that utilizes a particulate water-absorbing polymer whose acid groups are less than 50 mol % neutralized.

3. The process according to claim 1 that utilizes a particulate water-absorbing polymer whose acid groups are 15 to 45 mol % neutralized.

4. The process according to claim 1 that utilizes a particulate water-absorbing polymer whose acid groups are 15 to 40 mol % neutralized.

5. The process according to claim 1 that utilizes a polymer having a molar mass Mw of at least 500 as the amino-containing compound.

6. The process according to claim 1 wherein the amino-containing compound used is an addition polymer which contains vinylamine units and which is obtainable by partial or complete hydrolysis of a homo- or copolymer of N-vinylformamide.

7. The process according to claim 1 that utilizes polyvinylamine as the amino-containing compound.

8. The process according to claim 1 wherein the degree of neutralization of the acid-functional polymer after the treatment with amino-containing compound is in a range from 60 to 95 mol %.

9. The process according to claim 1 wherein the degree of neutralization of the acid-functional polymer after the treatment with the amino-containing compound is in a range from 65 to 85 mol %.

10. The process according to claim 1 wherein a particulate crosslinked polyacrylic acid having a degree of neutralization in the range from 15 to less than 50 mol % is mixed with cellulose fibers, and the mixture is treated with an amount of a compound containing vinylamine units such that the degree of neutralization of the acid-functional polymer is raised to 65-85 mol %.

11. The process according to claim 1 wherein the carrier material is selected from the group consisting of natural fibers, synthetic fibers, their blends, webs composed of said fibers and films/sheets.

* * * * *